United States Patent [19]

Larsen

[11] Patent Number: 4,998,415
[45] Date of Patent: Mar. 12, 1991

[54] BODY COOLING APPARATUS

[76] Inventor: John D. Larsen, 24303 Woolsey Canyon Rd., #135, Canoga Park, Calif. 91304

[21] Appl. No.: 428,914

[22] Filed: Oct. 30, 1989

[51] Int. Cl.$^5$ .............................................. F25D 23/12
[52] U.S. Cl. .................................... 62/231; 62/259.3; 62/457.9
[58] Field of Search ................. 62/231, 259.3, 457.9, 62/509

[56] References Cited

U.S. PATENT DOCUMENTS

| | | | |
|---|---|---|---|
| 2,933,904 | 4/1960 | Wellman | 62/509 |
| 2,984,994 | 5/1961 | Harkins | 62/259.3 X |
| 3,630,039 | 12/1971 | Hayashi | 62/259.3 X |
| 3,743,012 | 7/1973 | Laxo | 62/259.3 X |
| 3,916,911 | 11/1975 | Sauder et al. | 62/259.3 X |
| 4,170,998 | 10/1979 | Sauder | 62/259.3 X |

FOREIGN PATENT DOCUMENTS 8605088 9/1986 European Pat. Off. ........... 62/259.3

Primary Examiner—William E. Tapolcai
Attorney, Agent, or Firm—Edgar W. Averill, Jr.

[57] ABSTRACT

Body cooling apparatus for removing body or external heat in an environment where sufficient cooling by perspiration is not available. The apparatus includes a compressor and a condenser which feeds liquid coolant to a flexible tube network which is held adjacent the body to be cooled. The cooling takes place by the boiling of the liquid within the flexible tube network. The flow of liquid into the network is controlled depending upon the amount of cooling needed.

11 Claims, 2 Drawing Sheets

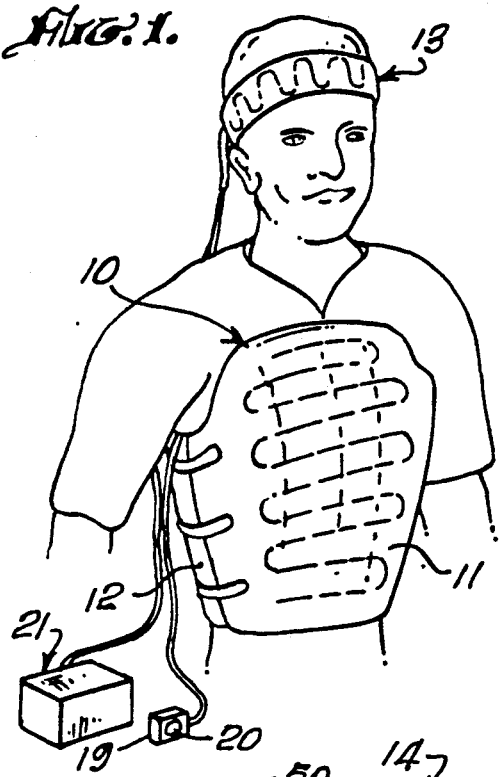
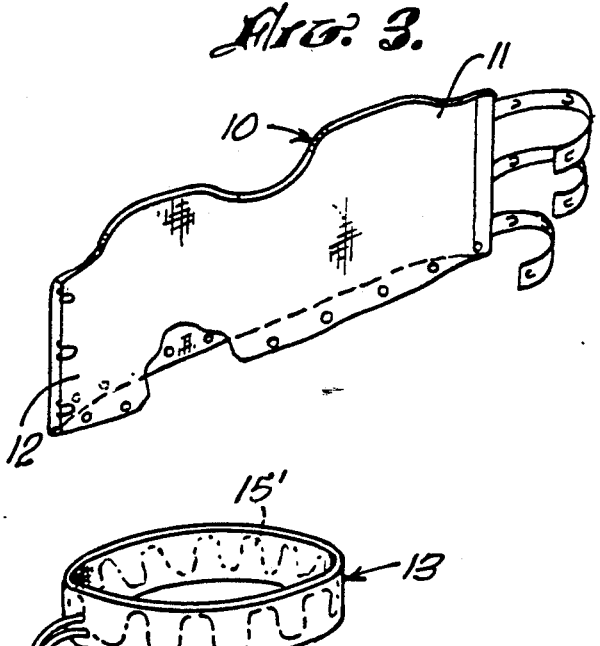
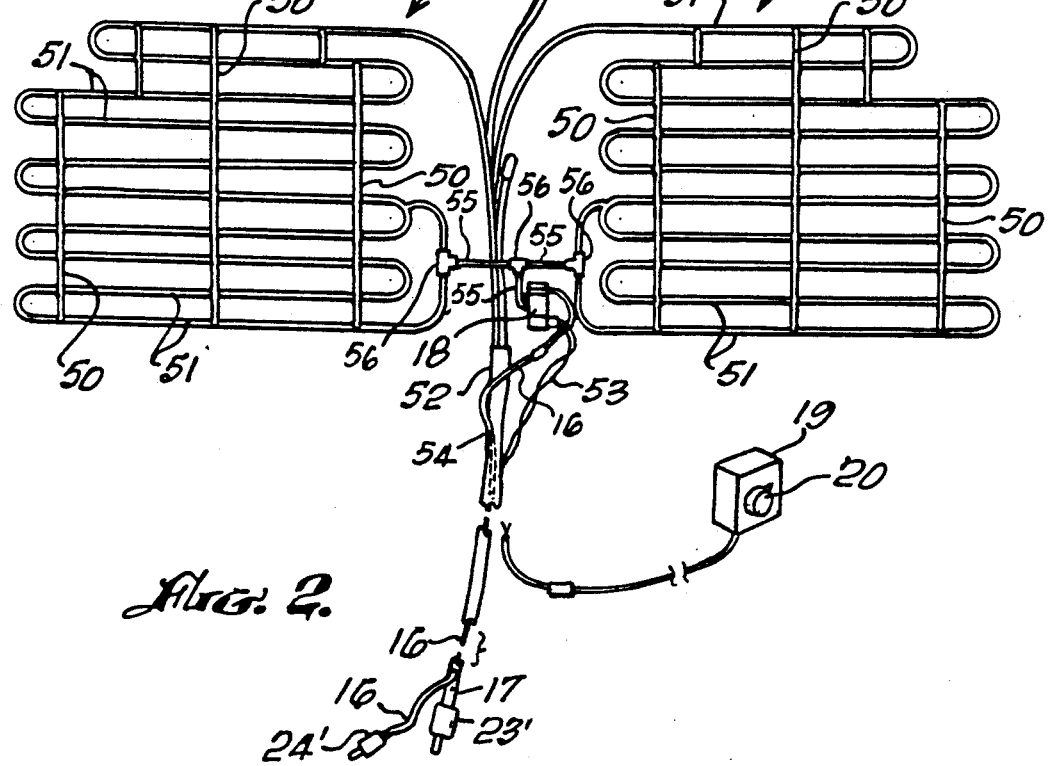

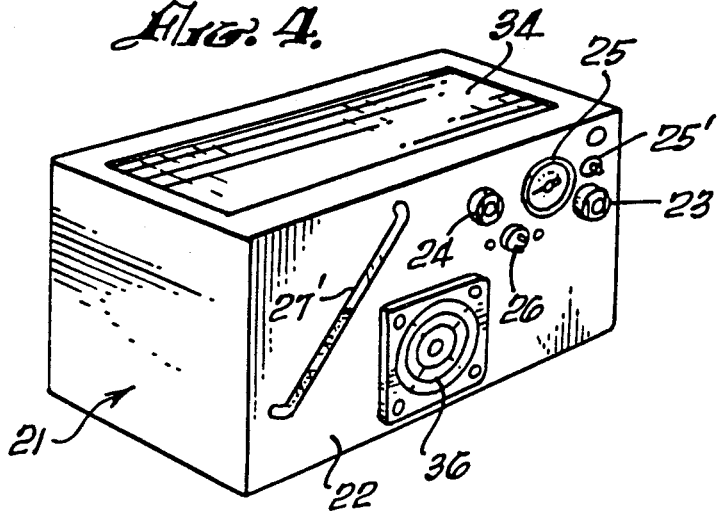
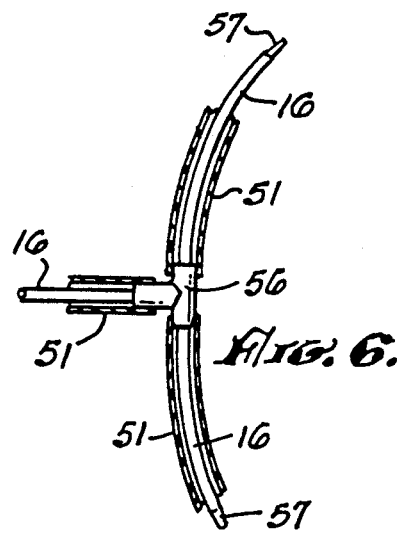
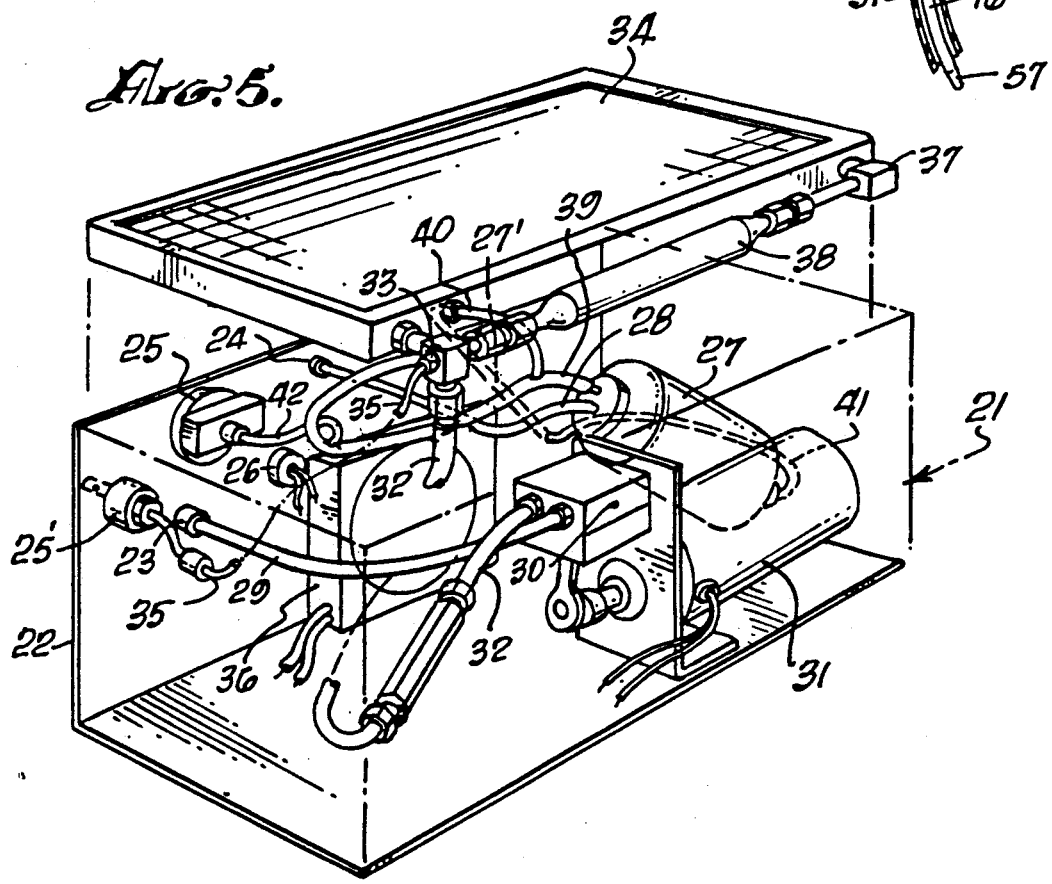

BODY COOLING APPARATUS

BACKGROUND OF THE INVENTION

The field of the invention is broadly refrigeration but it also relates to the control of body temperature.

The most common method for providing cooling to a person in a hot or unventilated area is to cool air by normal refrigeration and to pass the cooled air into an area adjacent the body to be cooled.

Liquid cooling apparatus is also known, and one such device is shown in the Jennings U.S. Pat. No. 3,289,748. A liquid, such as water, is passed through the tubes and then the liquid is cooled in a heat exchanger. Similarly, in the Feher U.S. Pat. No. 3,411,156, flexible tubing is provided for carrying a cooling liquid within a space garment. Another liquid-cooled garment is shown in the Crocker U.S. Pat. No. 3,430,688 where a pump and heat exchanger moves and cools the liquid passing through the tubing. In the Troyer U.S. Pat. No. 3,610,323, a garment has a tube therein, which tube includes capillaries. A chemical such as Freon is pumped into the tubes and escapes through the capillaries to evaporate and cause a cooling effect to the wearer. The Kramer U.S. Pat. No. 4,566,455 shows a scalp cover through which a coolant liquid is pumped. The coolant liquid is cooled by an ice and water mixture. In the Cahn U.S. Pat. No. 4,662,433, a blanket is provided with internal ducts through which a stable foam is circulated. The foam is heat exchanged with ice or an ice water reservoir or a cooled refrigerant. The Sauder U.S. Pat. No. 3,916,911 shows a cooling collar which includes a ductal metal coil, such as copper, through which a refrigerant such as Freon is circulated. Lastly, the Sauder U.S. Pat. No. 4,170,998 also shows a portable cooling apparatus which circulates a refrigerant through flexible tubing and from there into an auxiliary evaporator and back to a conventional compressor and condenser.

All of the above-discussed units are too bulky to be used in many confined situations such as a race car or within a suit completely sealed to handled toxic fumes. In this sort of an application, light weight and wearer comfort are very important.

SUMMARY OF THE INVENTION

It is, thus, an object of the present invention to provide a comfortable, lightweight, highly efficient body cooling apparatus.

The present invention is for a body cooling apparatus for removing body or external heat in an environment where sufficient cooling by perspiration is not available. The apparatus comprises a pressurized container containing a liquid having a vapor pressure at 120° Fahrenheit of below about seventy pounds and which has a boiling point of about 38° Fahrenheit at atmospheric pressure. The container has a liquid inlet connection and a liquid outlet connection. A flexible tube is connected to the liquid outlet connection of the pressurized container, and the flexible tube is connected to the inlet of a flexible tube network including an inlet and an outlet, said flexible tube network being held adjacent the body to be cooled, thereby heating the liquid and causing it to boil completely in the flexible tube network. The resulting gas is passed to a compressor and then to a condenser where it is condensed to a liquid and returned to the pressurized reservoir. A control valve is preferably provided to cycle the flow of liquid through the flexible tube network. Preferably, the flexible tube network is held in a lightweight vest, or other garment, so that the resulting apparatus permits a maximum of movement and a minimum of discomfort.

BRIEF DESCRIPTION OF THE DRAWINGS

FIG. 1 is a perspective view of the upper portion of a wearer wearing a vest and a head band containing flexible tube networks of the body cooling apparatus of the present invention.

FIG. 2 is a schematic view of the flexible tube network and inlet and control apparatus thereof of the body cooling apparatus of the present invention.

FIG. 3 is a perspective view of the vest shown in FIG. 1.

FIG. 4 is a perspective view of the exterior of the compressor, condenser and reservoir of the body cooling apparatus of the present invention.

FIG. 5 is an exploded perspective view, partially cut away, showing the internal components of the apparatus of FIG. 4.

FIG. 6 is an enlarged view of the fluid connection fittings between the apparatus of FIG. 4 and the flexible tube network of FIG. 2.

DESCRIPTION OF THE PREFERRED EMBODIMENTS

The body cooling apparatus of the present invention is preferably worn about the user as indicated in FIG. 1. In FIG. 1, the user is wearing a vest 10 which has a front half 11, a back half 12 and a headband 13. These three heat exchange elements each include a flexible tube network such as that indicated by reference characters 14, 15 and 15' in FIG. 2. Of course, other elements can be added to cool, for instance, the arms and thighs. Furthermore, the elements may be in the shape of a blanket for hospital use. Each of these three networks is fed with liquid refrigerant through a flexible tube 16 and returns after being vaporized in the flexible tube networks through a flexible tube 17. The flow of liquid is controlled by a control valve 18 which, in turn, is cycled into an open and closed configuration by a control box 19 including a control knob 20. The internal details of control box 19 are not shown since the unit need merely provide a timed cycled output. It is preferably powered by a nine-volt dry cell battery which permits a lightweight and yet long-life unit.

The internals of the lightweight compressor and condenser are shown best in FIGS. 4 and 5 of the drawings. The unit is held in a box, or frame, 21 which on its face 22 includes a liquid sight glass 27' which indicates the refrigerant level in the refrigerant reservoir. Also, a gas inlet fitting 23 and a liquid refrigerant outlet fitting 24 are positioned so that the fitting 24' on the flexible liquid-conducting tube 16 may be readily plugged into fitting 24, and fitting 23' at the end of the gas tube 17 may be readily plugged in the fitting 23. A pressure gage 25 indicates the system pressure in the liquid reservoir, and a connector 26 is used to supply the unit with twelve-volt electricity if used in a motor vehicle or other conventional storage battery. An air bleed fitting 25' is provided to remove air from the system.

In FIG. 5, the internal components of the unit of FIG. 4 may be readily seen. A pressurized container 27 contains liquid and gaseous refrigerant, the level of which is shown in sight glass 27'. The refrigerant is preferably a low boiling liquid sold under the trademark Freon R114. This has a pressure of fifty pounds per square inch gage at 120° Fahrenheit. In this way, even under relatively hot conditions, the refrigerant may still be easily retained in flexible plastic tubing such as polyurethane tubing. The important considerations are first that the liquid boil rapidly at about 100° Fahrenheit at atmospheric pressure and secondly that it not develop a vapor pressure of about seventy pounds at about 50° Fahrenheit. Under these conditions, the unit will cool the body rapidly and yet not require tubing with a large wall thickness which would reduce heat transfer.

In one example of a working unit, the flexible tube network has an inside diameter of approximately 40/1000 of an inch, and the larger gas tubing has an inside diameter of about ⅛th of an inch.

Returning now to FIG. 5, the liquid passes from pressurized container 27 through liquid outlet 28 to fitting 24. Gas returning from the flexible tube network enters through gas inlet fitting 23 where it passes through tube 29 to the inlet of a gas compressor 30. Gas compressor 30 operates at 3,000 rpm and is operated by a motor 31 and has a gas outlet 32 which passes through a fitting 33 to condenser 34. Fitting 33 also includes a capillary line 35 which passes to air bleed fitting 25'. Condenser 34 has a plurality of cooling fins and air is forced through condenser 34 by fan 36. Liquid passes out of condenser 34 through fitting 37 and into a filter 38. From filter 38, the liquid passes through a liquid inlet line 39 and into pressurized container 27. Sight glass 27' is connected to line 40 which, in turn, is connected to liquid inlet line 39. The other end of sight glass 27' is connected to line 41 which passes into the bottom of pressurized container 27. It should be noted that liquid outlet 28 has a tube which passes to near the bottom of pressurized container 27 so that liquid is fed from container 27 into liquid outlet 28. Pressure gage 25 is fed through line 42 which is connected to liquid inlet 39.

The entire unit weighs no more than about ten pounds and is thus vastly different from prior art units.

A typical control cycle would open control valve 18 for one second and turn it off for three seconds. Of course, the control of the fluid flow may be maintained by merely throttling the flow of liquid rather than cycling it in an on and off manner. The liquid refrigerant flows outwardly into tube 16. Tube 16 is preferably located within tube 52 as set forth below. Tube 16 exits tube 52 at 54 and enters control valve 18. When valve 18 is open, liquid refrigerant passes through lines 55 and tees 56 into the networks 14 and 15. A typical connection of the tube 16 with tube 51 is shown in FIG. 6. There it can be seen that the liquid containing tubes 16 are preferably narrowed at the end to provide nozzles 57 within tube 51. The particular construction of the flexible tube networks 14 and 15 has its integrity maintained by a plurality of vertical straps 50 which are adhered to the flexible tubing 51. These tubes are not connected internally but merely supply support to hold the tubing relatively evenly throughout vest halves 11 and 12. It has also been found beneficial to provide a coaxial tubing at the portion of the liquid inlet to the flexible tube network and the gaseous return indicated by reference character 52 in FIG. 2. In this way, heat is transferred between the incoming liquid and the returning gas to improve the efficiency of the operation. Furthermore, a single tube is much less likely to become entangled in use. Since one of the main advantages of the present invention is maneuverability, this single tube feature enhances that as well as improving heat transfer. The control box 19 may be connected to the control valve 18 by wires 53. These wires may be relatively short as the control box may be worn about the waist for easy access of the wearer.

The present embodiments of this invention are thus to be considered in all respects as illustrative and not restrictive; the scope of the invention being indicated by the appended claims rather than by the foregoing description. All changes which come within the meaning and range of equivalency of the claims are intended to be embraced therein.

What is claimed is:

1. Body cooling apparatus for removing body or external heat in an environment where sufficient cooling by perspiration is not available, said apparatus comprising:

a pressurized container containing a liquid having a vapor pressure at 120 Fahrenheit of below about seventy pounds and which has a boiling point at atmospheric pressure below about 50 Fahrenheit, said container having a liquid inlet connection and a liquid outlet connection;

a flexible tube connected to the liquid outlet connection of said pressurized container, said flexible tube connected to the inlet of a flexible tube network including an inlet and an outlet, said network having a plurality of liquid inlets and said network being held adjacent a body to be cooled, thereby heating the liquid and causing it to boil to cool the body and to vaporize the liquid into a gas;

a gas compressor for compressing said gas, said gas compressor including gas inlet and outlet lines, said inlet of said compressor being connected to said outlet of said network;

a condenser having a gas inlet and a liquid outlet line, said gas inlet of said condenser being connected to the gas outlet line of said compressor and the liquid outlet line of said condenser being connected to the liquid inlet of said pressurized container; and control valve means in said flexible tube connected to said liquid outlet connection of said pressurized container to control the flow of liquid into said network and to control the amount of cooling possible from said network, said control valve means comprising an electrically operated valve controlled by a clock providing an adjustable cycle of electric signal to turn said electrically operated valve on for a predetermined amount of time and to turn said valve off for a predetermined amount of time.

2. The body cooling apparatus of claim 1 wherein said flexible tube network is held in a fabric garment.

3. The body cooling apparatus of claim 2 wherein said fabric garment is a vest.

4. The body cooling apparatus of claim 2 wherein said garment is a head band.

5. The body cooling apparatus of claim 1 wherein said pressurized container, said gas compressor and said condenser are held in a frame, said frame including a liquid outlet fitting and a gas inlet fitting.

6. The body cooling apparatus of claim 1 wherein said flexible tube network is fabricated from tubing having an internal diameter of about one-eighth of an inch.

7. The body cooling apparatus of claim 6 wherein the liquid inlet line of said flexible tubing network is coaxially positioned within said gas outlet line of said flexible tubing network.

8. The body cooling apparatus of claim 1 wherein there are two separate flexible tubing networks each having a liquid inlet line and a gas outlet line and each of said flexible tubing networks being held in a vest.

9. Body cooling apparatus for removing body or external heat in an environment where sufficient cooling by perspiration is not available, said apparatus comprising:
   a pressurized container containing a liquid boiling at temperature of about 38° at atmospheric pressure, said container having a liquid inlet connection and a liquid outlet connection;
   a flexible tube connected to the liquid outlet connection of said pressurized container, said flexible tube connected to the inlet of a flexible tube network including an inlet and an outlet, said network being held adjacent a body to be cooled, thereby heating the liquid and causing it to boil to cool the body and to vaporize the liquid into a gas;
   a gas compressor for compressing said gas, said gas compressor including gas inlet and outlet lines, said inlet of said compressor being connected to said outlet of said network;
   a condenser having a gas inlet and a liquid outlet line, said gas inlet of said condenser being connected to the gas outlet line of said compressor and the liquid outlet line of said condenser being connected to the liquid inlet of said pressurized container, said pressurized container, said gas compressor and said condenser being held in a frame; and
   control valve means in said flexible tube connected to said liquid outlet connection of said pressurized container to control the flow of liquid into said network and to control the amount of cooling possible from said network, said control valve means including timing means to cycle the flow of liquid between an on and an off position, and the amount at time the valve is on and the amount of time the valve is off being controlled by a clock have an external adjustment control.

10. The body cooling apparatus of claim 9 wherein said frame further includes a pressure gage, a liquid level indicator and a cooling fan.

11. The body cooling apparatus of claim 10 wherein said apparatus is powered by a source of twelve-volt direct current.

* * * * *